US007202385B2

(12) United States Patent
Mueller et al.

(10) Patent No.: US 7,202,385 B2
(45) Date of Patent: Apr. 10, 2007

(54) PROCESS FOR THE ALKOXYLATION OF MONOOLS IN THE PRESENCE OF METALLO-ORGANIC FRAMEWORK MATERIALS

(75) Inventors: Ulrich Mueller, Neustadt (DE); Olga Metelkina, Ludwigshafen (DE); Michael Hesse, Worms (DE); Michael Stoesser, Neuhofen (DE); Peter Haas, Limburgerhof (DE); Omar Yaghi, Ann Arbor, MI (US)

(73) Assignees: BASF Aktiengesellschaft, Ludwigshafen (DE); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/285,070

(22) Filed: Nov. 23, 2005

(65) Prior Publication Data

US 2006/0135824 A1    Jun. 22, 2006

Related U.S. Application Data

(63) Continuation of application No. 10/611,863, filed on Jul. 3, 2003, now abandoned.

(51) Int. Cl.
    *C07C 41/03* (2006.01)
(52) U.S. Cl. .................. 568/679; 568/622; 521/50
(58) Field of Classification Search ............. 568/679, 568/622; 521/50
    See application file for complete search history.

(56) References Cited

U.S. PATENT DOCUMENTS

| 3,328,467 | A | 6/1967 | Hamilton |
| 3,651,152 | A | 3/1972 | Umbach et al. |
| 5,648,508 | A | 7/1997 | Yaghi |
| 6,348,607 | B1 | 2/2002 | Muller et al. |
| 6,479,680 | B1 | 11/2002 | Bassler et al. |
| 6,518,441 | B2 | 2/2003 | Grosch et al. |
| 6,617,467 | B1 | 9/2003 | Mueller et al. |
| 6,624,318 | B1 | 9/2003 | Mueller et al. |
| 2003/0050487 | A1 | 3/2003 | Muller et al. |
| 2003/0078311 | A1 | 4/2003 | Muller et al. |
| 2003/0148165 | A1 | 8/2003 | Muller et al. |
| 2003/0222023 | A1 | 12/2003 | Mueller et al. |
| 2004/0081611 | A1 | 4/2004 | Muller et al. |
| 2004/0097724 | A1 | 5/2004 | Muller et al. |

FOREIGN PATENT DOCUMENTS

| CA | 2 387 122 | 2/2001 |
| CA | 2 414 756 | 1/2003 |
| CA | 2 414 779 | 1/2003 |
| DE | 197 23 950 | 12/1998 |
| DE | 198 35 907 | 2/2000 |
| DE | 198 47 629 | 4/2000 |
| DE | 199 36 547 | 2/2001 |
| DE | 100 15 246 | 10/2001 |
| DE | 100 32 884 | 1/2002 |
| DE | 101 11 230 | 8/2002 |
| EP | 0 557 116 | 8/1993 |
| EP | 0 790 253 | 8/1997 |
| WO | 02/088148 | 11/2002 |

OTHER PUBLICATIONS

M. O'Keeffe, et al., Journal of Solid State Chemistry, vol. 152, pp. 3-20, "Section 1: Tutorial Frameworks for Extended Solids: Geometrical Design Principles", 2000.
H. Li, et al., Letters to Nature, vol. 402, pp. 276-279, "Design and Synthesis of an Exceptionally Stable and Highly Porous Metal-Organic Framework", Nov. 18, 1999.
M. Eddaoudia, et al., Topics in Catalysis, vol. 9, pp. 105-111, "Design and Synthesis of Metal-Carboxylate Frameworks With Permanent Microporosity", 1999.
B. Chen, et al., Science, vol. 291, pp. 1021-1023, "Interwoven Metal-Organic Framework on a Periodic Minimal Surface With Extra-Large Pores", Feb. 9, 2001.
H. Buttner, Pure & Applied Chem, vol. 45 pp. 69-73, "The International Federation of Clinical Chemistry (IFCC) and Reference Methods", 1976.
M. Eddaoudi, et al., Science, vol. 295, pp. 469-472, "Systematic Design of Pore Size and Functionality in Isoreticular MOFs and Their Application in Methane Storage", Jan. 18, 2002.

*Primary Examiner*—Rosalynd Keys
(74) *Attorney, Agent, or Firm*—Oblon, Spivak, McClelland, Maier & Neustadt, P.C.

(57) ABSTRACT

The present invention relates to a process for the alkoxylation of a monool with at least one alkoxylating agent to an alkoxylated alcohol wherein a catalyst is employed which comprises a metallo-organic framework material of metal ions and at least bidentate coordinately bound organic ligands.

8 Claims, No Drawings

PROCESS FOR THE ALKOXYLATION OF MONOOLS IN THE PRESENCE OF METALLO-ORGANIC FRAMEWORK MATERIALS

The present application is a continuation application of U.S. Ser. No. 10/611,863, filed on Jul. 3, 2003, which is abandoned.

The present invention relates to a process for the alkoxylation of monools in the presence of catalyst systems comprising a porous metallo-organic framework material of metal ions and a coordinately bound organic ligand which is at least bidentate. The invention further encompasses the use of polyoxyalkylene alcohols obtained in the process according to the present invention as tensides and flotation oils.

Polyoxyalkylene alcohols can be prepared e.g. by way of base or acid catalyzed polyaddition of alkaline oxides to polyfunctional organic compounds (starters). Suitable starters are e.g. water, alcohols, acids or amines or mixtures thereof which are selected according to the alcohol to be prepared. The drawback of the known preparation methods is that several elaborate purifying steps are necessary in order to separate the catalyst residue from the reaction product. Furthermore, the processes known in the art result in a mixture of various alkoxylation products, ranging from mono- to polyalkoxylated alcohols.

One object of the invention is to provide a process for the preparation of polyoxyalkylene alcohols from monools which does not show the drawbacks of the processes known in the art. In particular, the thus-obtained polyoxyalkylene alcohols should have a low impurity content, without requiring elaborate purifying steps of the starting materials and/or intermediate products. The process should furthermore not require elaborate purification steps in order to separate the catalyst from the reaction product(s). In particular, the process should give defined alkoxylation products with a defined alkoxylation range.

These objects are solved by a process for the alkoxylation of a monool with at least one alkoxylating agent to a polyoxyalkylene alcohol wherein a catalyst is employed which comprises a metallo-organic framework material of metal ions and at least bidentate coordinately bound organic ligands.

The present invention is drawn towards the alkoxylation of monools which are reacted with an alkoxylating agent, in general an alkylene oxide. Examples for monools which lend themselves for an alkoxylation according to the present invention are known to the person skilled in the art. Examples include monools of linear and branched alkyl groups having 1 to 30, preferably 1 to 20, in particular 1 to 15 carbon atoms, which alkyl groups may carry one or more aryl substituents, of homo- and polynuclear aromatic groups having 4 to 30, preferably 4 to 20, in particular 1 to 10 carbon atoms, which aromatic groups may carry one or more alkyl substituents, and of linear and branched alkenyl groups having 2 to 30, preferably 2 to 20, in particular 2 to 15 carbon atoms and which alkenyl groups may carry one or more aryl substituents. The alkyl, alkenyl and aryl groups may contain one or more hetero atoms in their carbon skeleton, and all said groups may carry one or more substituents other than those named. Examples for hetero atoms include N, O and S. Examples for substituents include halides and pseudohalides. Preferred alcohols should be liquid at room temperature.

Examples for preferred alcohols include Propylheptanol, Tridecanol H und Tridecanol N.

The alkoxylating agent is in general selected from epoxides having two to 30 carbon atoms and mixtures of two or more thereof. Preferably a linear or branched, cyclic or non-cyclic alkylene oxide having two to 24 C-atoms optionally carrying one or more substituents from the group consisting of aromatic groups, halides, hydroxyl groups, silyl groups, non-cyclic ether and ammonium groups is employed.

For the preferred group of alkylene oxides, the following are cited by way of example: ethylene oxide, 1,2-epoxypropane, 1,2-epoxy-2-methylpropane, 1,2-epoxybutane, 2,3-epoxybutane, 1,2-epoxy-3-methylbutane, 1,2-epoxypentane, 1,2-epoxy-3-methylpentane, 1,2-epoxyhexane, 1,2-epoxyheptane, 1,2-epoxyoctane, 1,2-epoxynonane, 1,2-epoxydecane, 1,2-epoxyundecane, 1,2-epoxydodecane, 1,2-epoxycyclopentane, 1,2-epoxycyclohexane, (2,3-epoxypropyl) benzene, vinyloxirane, 3-phenoxy-1,2-epoxypropane, 2,3-epoxymethyl ether, 2,3-epoxylethyl ether, 2,3-epoxyl isopropyl ether, 2,3-epoxyl-1-propanol, (3,4-epoxybutyl) stearate, 4,5-epoxypentylacetate, 2,3-epoxy propane methacrylate, 2,3-epoxy propane acrylat, glycidylbutyrate, methylglycidate, ethyl-2,3-epoxybutanoate, 4-(trimethylsilyl) butane-1,2-epoxide, 4-(triethylsilyl)butane-1,2-epoxide, 3-(perfluoromethyl)propane oxide, 3-(perfluoroethyl)propane oxide, 3-(perfluorobutyl)propane oxide, 4-(2,3-epoxypropyl)morpholine, 1-(oxirane-2-ylmethyl)pyrrolidin-2-one, styrene oxide, vinyl oxirane, aliphatic 1,2-alkylene oxides having 5 to 24 C-atoms, cyclopentane oxide, cyclohexane oxide, cyclododecatriane-(1,5,9)-monoxide and mixtures of two or more of the compounds cited.

Particularly preferred in the context of the present invention are ethylene oxide, propylene oxide, 1,2-epoxybutane, 2,3-epoxybutane, 1,2-epoxy-2-methylpropane, styrene oxide, vinyloxirane and any mixtures of two or more of the compounds cited. The most preferred epoxides are ethylene oxide, propylene oxide and mixtures of ethylene oxide with propylene oxide.

The process of preparing an epoxide by epoxidation is hereinafter described in detail by way of example, referring to propylene oxide.

Propylene oxide can be obtained by reacting propylene with oxygen; hydrogen and oxygen; hydrogen peroxide; organic hydroperoxides; or halohydrines, preferably by reacting propylene with hydrogen peroxide, more preferred by reacting propylene with hydrogen peroxide in the presence of a catalyst comprising a zeolithic material, particularly by reacting propylene with hydrogen peroxide in the presence of a catalyst comprising a titanium-containing zeolithic material having CS-1-structure.

It is particularly suitable to use hydrogen peroxide for the epoxidation.

The epoxidation is in principle known from e.g. DE 100 55 652.3 and further patent applications of the present applicant, such as DE 100 32 885.7, DE 100 32 884.9, DE 100 15 246.5, DE 199 36 547.4, DE 199 26 725.1, DE 198 47 629.9, DE 198 35 907.1, DE 197 23 950.1, the content of which fully encompassed in the present application.

The alkoxylating agent obtained in the epoxidation step may be directly used without further treatment. It is, however, also possible within the present invention that the alkoxylating agent is treated beforehand, e.g. purified. As the purification method, mention can be made of a fine distillation. Suitable processes are e.g. disclosed in EP-B 0 557 116.

According to the present invention the alkoxylation reaction is carried out in the presence of a catalyst system which comprises a so called metallo-organic framework material.

Metal-organic framwork materials are known as such. They are described in, for example, U.S. Pat. No. 5,648,508, EP-A-0 709 253, M. O'Keeffe et al., J. Sol. State Chm., 152 (2000) p. 3–20, H. Li et al., Nature 402 (1999) p. 276 seq., M. Eddaoudi et al., Topics in Catalysis 9 (1999) p. 105–111, B. Chen. Et al., Science 291 (2001) p. 1021–23. An inexpensive way for the preparation of said materials is disclosed in DE 101 11 230.0. The preparation of isoreticular MoF's is disclosed in WO 02/088148. The content of the above-mentioned publications and applications to which reference is made herein, is fully incorporated in present application.

The metal-organic framework materials, as used in the present invention, comprise pores, particularly micro- and/or mesopores. Micropores are defined as pores having a diameter of 2 nm or below and mesopores as being pores having a diameter in the range of above 2 nm to 50 nm, respectively, according to the definition given in Pure Applied Chem. 45, p. 71 seq., particularly on p. 79 (1976). The presence of the micro- and/or mesopores can be monitored by sorption measurements for determining the capacity of the metal-organic framework materials to take up nitrogen at 77 K according to DIN 66131 and/or DIN 66134. The specific surface areas cited in the context of the present invention are always determined according to DIN 66131 and/or DIN 66134.

For example, a type-1-form of the isothermal curve indicates the presence of micropores [see, for example, paragraph 4 of M. Eddaoudi et al., Topics in Catalysis 9 (1999)]. In a preferred embodiment, the specific surface area, as calculated according to the Langmuir model (DIN 66131, 66134) preferably is above 5 $m^2/g$, further preferred above 10 $m^2/g$, more preferably above 50 $m^2/g$, particularly preferred above 500 $m^2/g$ and may increase to values of 3000 $m^2/g$.

The metal ions forming the metal-organic framework material employed according to the present invention are preferably selected from the groups Ia, IIIa, IIIa, IVa to VIIIa and Ib to VIb of the periodic system of the elements. Among these metals, particular reference is made to Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, and Bi, more preferably Zn, Cu, Ni, Pd, Pt, Ru, Rh and Co. With respect to the metal ions of the aforementioned elements, particular reference is made to: $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $OS^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$ and $Bi^+$.

With regard to the preferred metal ions and further details regarding the same, we particularly refer to: EP-A 0 790 253, particularly p. 10, l. 8–30, section "The Metal Ions", which section is incorporated herein by reference.

In addition to the metal salts disclosed in EP-A 0 790 253 and U.S. Pat. No. 5,648,508, other metallic compounds can be used, such as sulfates, phosphates and other compolex counter-ion metal salts of the main- and subgroup metals of the periodic system of the elements. Metal oxides, mixed oxides and mixutres of metal oxides and/or mixed oxides with or without a defined stoichiometry are preferred. All of the above mentioned metal compounds can be soluble or insoluble and they may be used as starting material either in form of a powder or as a shaped body or as any combination thereof.

The at least bidentate organic ligands present in the metall-organic framework material are capable of coordinating to the metal ion. Such ligands are known to the person skilled in the art. The at least bidentate organic ligand, is preferably selected from:
i) alkyl groups having from 1 to 10 carbon atoms,
ii) aryl groups having from 1 to 5 phenyl rings,
iii) alkyl and aryl amines carrying one or more alkyl groups having from 1 to 10 carbon atoms and/or one or more aryl groups having from 1 to 5 phenyl rings, which are covalently substituted by at least one functional group X which can coordinately bind to the metal ion and which is selected from the group consisting of $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_3$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, wherein R is an alkyl group having from 1 to 5 carbon atoms, or an aryl group consisting of 1 to 2 phenyl rings, and $CH(SH)_2$, $C(SH)_3$, $CH(NH_2)_2$, $C(NH_2)_2$, $CH(OH)_2$, $C(OH)_3$, $CH(CN)_2$ and $C(CN)_3$. WO 02/088148 discloses bidentate organic ligand from the group of aromatic compounds which can carry one or more substituents. The content of WO 02/088148, pages 8–14 is herein fully incorporated by reference.

Particularly to be mentioned are substituted and unsubstituted aliphatic α, ω-dicarboxylic acids, substituted or unsubstituted, mono- or polynuclear aromatic di-, tri- and tetracarboxylic acids and substituted or unsubstituted, aromatic di-, tri- and tetracarboxylic acids, having one or more nuclei, and carying at least one hetero atom Preferred ligands are selected from 1,3,5-benzene tricarboxylic acid (BCT), NDC (naphthalene dicarboxylate), BDC (benzene dicarboxylate), BTC (benzene tricarboxylate), BTB (benzene tribenzoate), and DHBC (2,5-dihydroxyterephtalic acid).

DHBC is the most preferred ligand. Besides the at least bidentate organic ligand, the framework material as used in accordance with the present invention may also comprise one or more monodentate ligands, which are preferably selected from the following monodentate substances and/or derivatives thereof:
a. alkyl amines and their corresponding alkyl ammonium salts, containing linear, branched, or cyclic aliphatic groups, having from 1 to 20 carbon atoms (and their corresponding ammonium salts);
b. aryl amines and their corresponding aryl ammonium salts having from 1 to 5 phenyl rings;
c. alkyl phosphonium salts, containing linear, branched, or cyclic aliphatic groups, having from 1 to 20 carbon atoms;
d. aryl phosphonium salts, having from 1 to 5 phenyl rings;
e. alkyl organic acids and the corresponding alkyl organic anions (and salts) containing linear, branched, or cyclic aliphatic groups, having from 1 to 20 carbon atoms;
f. aryl organic acids and their corresponding aryl organic anions and salts, having from 1 to 5 phenyl rings;
g. aliphatic alcohols, containing linear, branched, or cyclic aliphatic groups, having from 1 to 20 carbon atoms;
h. aryl alcohols having from 1 to 5 phenyl rings;
i. inorganic anions from the group consisting of:
   sulfate, nitrate, nitrite, sulfite, bisulfite, phosphate, hydrogen phosphate, dihydrogen phosphate, diphosphate, triphosphate, phosphate, phosphite, chloride, chlorate, bromide, bromate, iodide, iodate, carbonate, bicarbonate, and the corresponding acids and salts of the aforementioned inorganic anions, j. ammonia, carbon dioxide, methane, oxygen, ethylene, hexane, benzene, toluene, xylene, chlorobenzene, nitrobenzene, naphthalene, thiophene, pyridine, acetone, 1-2-dichloroethane, methylenechloride, tetrahydrofuran, ehtanolamine, triethylamine and trifluoromethylsulfonic acid.

Further details regarding the at least bidentate organic ligand and the mono-dentate substances, from which the ligands of the framework material as used in the present application are derived, may be deduced from EP-A 0 790 253, whose respective content is incorporated into the present application by reference.

Within the present application, framework materials of the kind described herein, which comprise $Zn^{2+}$ as a metal ion and ligands derived from terephthalic acid as the bidentate ligand, are particularly preferred.

Further metal ions, at least bidentate and monodentats organic ligands which are useful for the preparation of the framework materials used in the present invention as well as processes for their preparation are particularly disclosed in EP-A 0 790 253, U.S. Pat. No. 5,648,508 and DE 10111230.0.

As solvents, which are particularly useful for the preparation of MOF-5, in addition to the solvents disclosed in the above-referenced literature dimethyl formamide, diethyl formamide and N-methylpyrrolidone, alone, in combination with each other or in combination with other solvents may be used. Within the preparation of the framework materials, particularly within the preparation of MOF-5, the solvents and mother liquors can be recycled after crystallization.

The pore sizes of the metal-organic framework can be adjusted by selecting suitable bidendate ligands (=linkers). Generally, the larger the linker, the larger the pore size. Any pore size that is still supported by a the metal-organic framework in the absence of a host and at temperatures of at least 200° C. is conceivable. Pore sizes ranging from 0,2 nm to 30 nm are preferred, with pore sizes ranging from 0,3 nm to 3 nm being particularly preferred.

In the following, examples of metal-organic framework materials (MOFs) are given to illustrate the general concept given above. These specific examples, however, are not intended to limit the scope of the present invention.

By way of example, a list of metal-organic framework materials already synthesized and characterized is given below. This also includes novel isoreticular metal organic framework materials (IR-MOFs), which may be used in the context of the present application. Such materials having the same framework topology while displaying different pore sizes and crystal densities are described, for example in M. Eddouadi et al., *Science* 295 (2002) 469, whose respective content is incorporated into the present application by reference.

The solvents used are of particular importance for the synthesis of these materials and are therefore mentioned in the table. The values for the cell parameters (angles Δ, E and θ as well as the spacings a, b and c, given in Angstrom) have been obtained by x-ray diffraction and represent the space group given in the table as well.

| MOF-n | Ingredients molar ratios M + L | Solvents | α | β | γ | a | b | c | Space Group |
|---|---|---|---|---|---|---|---|---|---|
| MOF-0 | $Zn(NO_3)_2.6H_2O$ $H_3(BTC)$ | Ethanol | 90 | 90 | 120 | 16.711 | 16.711 | 14.189 | P6(3)/Mcm |
| MOF-2 | $Zn(NO_3)_2.6H_2O$ (0.246 mmol) $H_2(BDC)$ 0.241 mmol) | DMF Toluene | 90 | 102.8 | 90 | 6.718 | 15.49 | 12.43 | P2(1)/n |
| MOF-3 | $Zn(NO_3)_2.6H_2O$ (1.89 mmol) $H_2(BDC)$ (1.93 mmol) | DMF MeOH | 99.72 | 111.11 | 108.4 | 9.726 | 9.911 | 10.45 | P-1 |
| MOF-4 | $Zn(NO_3)_2.6H_2O$ (1.00 mmol) $H_3(BTC)$ (0.5 mmol) | Ethanol | 90 | 90 | 90 | 14.728 | 14.728 | 14.728 | P2(1)3 |
| MOF-5 | $Zn(NO_3)_2.6H_2O$ (2.22 mmol) $H_2(BDC)$ (2.17 mmol) | DMF Chlorobenzene | 90 | 90 | 90 | 25.669 | 25.669 | 25.669 | Fm-3m |
| MOF-38 | $Zn(NO_3)_2.6H_2O$ (0.27 mmol) $H_3(BTC)$ (0.15 mmol) | DMF Chlorobenzene | 90 | 90 | 90 | 20.657 | 20.657 | 17.84 | I4cm |
| MOF-31 $Zn(ADC)_2$ | $Zn(NO_3)_2.6H_2O$ 0.4 mmol $H_2(ADC)$ 0.8 mmol | Ethanol | 90 | 90 | 90 | 10.821 | 10.821 | 10.821 | Pn(-3)m |
| MOF-12 $Zn_2(ATC)$ | $Zn(NO_3)_2.6H_2O$ 0.3 mmol $H_4(ATC)$ 0.15 mmol | Ethanol | 90 | 90 | 90 | 15.745 | 16.907 | 18.167 | Pbca |
| MOF-20 ZnNDC | $Zn(NO_3)_2.6H_2O$ 0.37 mmol $H_2NDC$ 0.36 mmol | DMF Chlorobenzene | 90 | 92.13 | 90 | 8.13 | 16.444 | 12.807 | P2(1)/c |
| MOF-37 | $Zn(NO_3)_2.6H_2O$ 0.2 mmol | DEF Chlorobenzene | 72.38 | 83.16 | 84.33 | 9.952 | 11.576 | 15.556 | P-1 |

-continued

| MOF-n | Ingredients molar ratios M + L | Solvents | α | β | γ | a | b | c | Space Group |
|---|---|---|---|---|---|---|---|---|---|
| MOF-8 Tb₂ (ADC) | H₂NDC 0.2 mmol Tb(NO₃)₃.5H₂O 0.10 mmol | DMSO MeOH | 90 | 115.7 | 90 | 19.83 | 9.822 | 19.183 | C2/c |
| MOF-9 Tb₂ (ADC) | H₂ADC 0.20 mmol Tb(NO₃)₃.5H₂O 0.08 mmol | DMSO | 90 | 102.09 | 90 | 27.056 | 16.795 | 28.139 | C2/c |
| MOF-6 | H₂ADB 0.12 mmol Tb(NO₃)₃.5H₂O 0.30 mmol H₂ (BDC) 0.30 mmol | DMF MeOH | 90 | 91.28 | 90 | 17.599 | 19.996 | 10.545 | P21/c |
| MOF-7 | Tb(NO₃)₃.5H₂O 0.15 mmol H₂(BDC) 0.15 mmol | H₂O | 102.3 | 91.12 | 101.5 | 6.142 | 10.069 | 10.096 | P-1 |
| MOF-69A | Zn(NO₃)₂.6H₂O 0.083 mmol 4,4'BPDC 0.041 mmol | DEF H₂O₂ MeNH₂ | 90 | 111.6 | 90 | 23.12 | 20.92 | 12 | C2/c |
| MOF-69B | Zn(NO₃)₂.6H₂O 0.083 mmol 2,6-NCD 0.041 mmol | DEF H₂O₂ MeNH₂ | 90 | 95.3 | 90 | 20.17 | 18.55 | 12.16 | C2/c |
| MOF-11 Cu₂(ATC) | Cu(NO₃)₂.2.5H₂O 0.47 mmol H₂ATC 0.22 mmol | H₂O | 90 | 93.86 | 90 | 12.987 | 11.22 | 11.336 | C2/c |
| MOF-11 Cu₂(ATC) dehydr. | | | 90 | 90 | 90 | 8.4671 | 8.4671 | 14.44 | P42/mmc |
| MOF-14 Cu₃ (BTB) | Cu(NO₃)₂.2.5H₂O 0.28 mmol H₃BTB 0.052 mmol | H₂O DMF EtOH | 90 | 90 | 90 | 26.946 | 26.946 | 26.946 | Im-3 |
| MOF-32 Cd(ATC) | Cd(NO₃)₂.4H₂O 0.24 mmol H₄ATC 0.10 mmol | H₂O NaOH | 90 | 90 | 90 | 13.468 | 13.468 | 13.468 | P(-4)3m |
| MOF-33 Zn₂ (ATB) | ZnCl₂ 0.15 mmol H₄ATB 0.02 mmol | H₂O DMF EtOH | 90 | 90 | 90 | 19.561 | 15.255 | 23.404 | Imma |
| MOF-34 Ni(ATC) | Ni(NO₃)₂.6H₂O 0.24 mmol H₄ATC 0.10 mmol | H₂O NaOH | 90 | 90 | 90 | 10.066 | 11.163 | 19.201 | P2₁2₁2₁ |
| MOF-36 Zn₂ (MTB) | Zn(NO₃)₂.4H₂O 0.20 mmol H₄MTB 0.04 mmol | H₂O DMF | 90 | 90 | 90 | 15.745 | 16.907 | 18.167 | Pbca |
| MOF-39 Zn₃O(HBTB) | Zn(NO₃)₂ 4H₂O 0.27 mmol H₃BTB 0.07 mmol | H₂O DMF EtOH | 90 | 90 | 90 | 17.158 | 21.591 | 25.308 | Pnma |
| NO305 | FeCl₂.4H₂O 5.03 mmol formic acid 86.90 mmol | DMF | 90 | 90 | 120 | 8.2692 | 8.2692 | 63.566 | R-3c |
| NO306A | FeCl₂.4H₂O 5.03 mmol formic acid 86.90 mmol | DEF | 90 | 90 | 90 | 9.9364 | 18.374 | 18.374 | Pbcn |
| NO29 MOF-0 like | Mn(Ac)₂.4H₂O 0.46 mmol H₃BTC 0.69 mmol | DMF | 120 | 90 | 90 | 14.16 | 33.521 | 33.521 | P-1 |
| BPR48 A2 | Zn(NO₃)₂ 6H₂O 0.012 mmol H₂BDC 0.012 mmol | DMSO Toluene | 90 | 90 | 90 | 14.5 | 17.04 | 18.02 | Pbca |
| BPR69 B1 | Cd(NO₃)₂ 4H₂O 0.0212 mmol | DMSO | 90 | 98.76 | 90 | 14.16 | 15.72 | 17.66 | Cc |

-continued

| MOF-n | Ingredients molar ratios M + L | Solvents | α | β | γ | a | b | c | Space Group |
|---|---|---|---|---|---|---|---|---|---|
| BPR92 A2 | H$_2$BDC 0.0428 mmol Co(NO$_3$)$_2$.6H$_2$O 0.018 mmol | NMP | 106.3 | 107.63 | 107.2 | 7.5308 | 10.942 | 11.025 | P1 |
| BPR95 C5 | H$_2$BDC 0.018 mmol Cd(NO$_3$)$_2$ 4H$_2$O 0.012 mmol | NMP | 90 | 112.8 | 90 | 14.460 | 11.085 | 15.829 | P2(1)/n |
| CuC$_6$H$_4$O$_6$ | H$_2$BDC 0.36 mmol Cu(NO$_3$)$_2$.2.5H$_2$O 0.370 mmol | DMF Chlorobenzene | 90 | 105.29 | 90 | 15.259 | 14.816 | 14.13 | P2(1)/c |
| M(BTC) MOF-0like | H$_2$BDC(OH)$_2$ 0.37 mmol Co(SO$_4$) H$_2$O 0.055 mmol | DMF | | Same as MOF-0 | | | | | |
| Tb(C$_6$H$_4$O$_6$) | H$_3$BTC 0.037 mmol Tb(NO$_3$)$_3$.5H$_2$O 0.370 mmol H$_2$(C$_6$H$_4$O$_6$) 0.56 mmol | DMF chlorobenzene | 104.6 | 107.9 | 97.147 | 10.491 | 10.981 | 12.541 | P-1 |
| Zn(C$_2$O$_4$) | ZnCl$_2$ 0.370 mmol oxalic acid 0.37 mmol | DMF chlorobenzene | 90 | 120 | 90 | 9.4168 | 9.4168 | 8.464 | P(−3)1m |
| Co(CHO) | Co(NO$_3$)$_2$.5H$_2$O 0.043 mmol formic acid 1.60 mmol | DMF | 90 | 91.32 | 90 | 11.328 | 10.049 | 14.854 | P2(1)/n |
| Cd(CHO) | Cd(NO$_3$)$_2$.4H$_2$O 0.185 mmol formic acid 0.185 mmol | DMF | 90 | 120 | 90 | 8.5168 | 8.5168 | 22.674 | R-3c |
| Cu(C$_3$H$_2$O$_4$) | Cu(NO$_3$)$_2$.2.5H$_2$O 0.043 mmol malonic acid 0.192 mmol | DMF | 90 | 90 | 90 | 8.366 | 8.366 | 11.919 | P43 |
| Zn$_6$(NDC)$_5$ MOF-48 | Zn(NO$_3$)$_2$.6H$_2$O 0.097 mmol 14 NDC 0.069 mmol | DMF chlorobenzene H$_2$O$_2$ | 90 | 95.902 | 90 | 19.504 | 16.482 | 14.64 | C2/m |
| MOF-47 | Zn(NO$_3$)$_2$ 6H$_2$O 0.185 mmol H$_2$(BDC[CH$_3$]$_4$) 0.185 mmol | DMF Chlorobenzene H$_2$O$_2$ | 90 | 92.55 | 90 | 11.303 | 16.029 | 17.535 | P2(1)/c |
| MO25 | Cu(NO$_3$)$_2$.2.5H$_2$O 0.084 mmol BPhDC 0.085 mmol | DMF | 90 | 112.0 | 90 | 23.880 | 16.834 | 18.389 | P2(1)/c |
| Cu-Thio | Cu(NO$_3$)$_2$.2.5H$_2$O 0.084 mmol thiophene dicarboxylic 0.085 mmol | DEF | 90 | 113.6 | 90 | 15.4747 | 14.514 | 14.032 | P2(1)/c |
| CIBDC1 | Cu(NO$_3$)$_2$.2.5H$_2$O 0.084 mmol H$_2$(BDCCl$_2$) 0.085 mmol | DMF | 90 | 105.6 | 90 | 14.911 | 15.622 | 18.413 | C2/c |
| MOF-101 | Cu(NO$_3$)$_2$.2.5H$_2$O 0.084 mmol BrBDC 0.085 mmol | DMF | 90 | 90 | 90 | 21.607 | 20.607 | 20.073 | Fm3m |
| Zn$_3$(BTC)$_2$ | ZnCl$_2$ 0.033 mmol H$_3$BTC 0.033 mmol | DMF EtOH Base Added | 90 | 90 | 90 | 26.572 | 26.572 | 26.572 | Fm-3m |
| MOF-j | Co(CH$_3$CO$_2$)$_2$.4H$_2$O (1.65 mmol) H$_3$(BZC) (0.95 mmol) | H$_2$O | 90 | 112.0 | 90 | 17.482 | 12.963 | 6.559 | C2 |
| MOF-n | Zn(NO$_3$)$_2$.6H$_2$O H$_3$(BTC) | ethanol | 90 | 90 | 120 | 16.711 | 16.711 | 14.189 | P6(3)/mcm |
| PbBDC | Pb(NO$_3$)$_2$ (0.181 mmol) H$_2$(BDC) | DMF Ethanol | 90 | 102.7 | 90 | 8.3639 | 17.991 | 9.9617 | P2(1)/n |

| MOF-n | Ingredients molar ratios M + L | Solvents | α | β | γ | a | b | c | Space Group |
|---|---|---|---|---|---|---|---|---|---|
| Znhex | (0.181 mmol) Zn(NO$_3$)$_2$.6H$_2$O (0.171 mmol) H$_3$BTB (0.114 mmol) | DMF p-xylene ethanol | 90 | 90 | 120 | 37.1165 | 37.117 | 30.019 | P3(1)c |
| AS16 | FeBr$_2$ 0.927 mmol H$_2$(BDC) 0.927 mmol | DMF anhydr. | 90 | 90.13 | 90 | 7.2595 | 8.7894 | 19.484 | P2(1)c |
| AS27-2 | FeBr$_2$ 0.927 mmol H$_3$(BDC) 0.464 mmol | DMF anhydr. | 90 | 90 | 90 | 26.735 | 26.735 | 26.735 | Fm3m |
| AS32 | FeCl$_3$ 1.23 mmol H$_2$(BDC) 1.23 mmol | DMF anhydr. Ethanol | 90 | 90 | 120 | 12.535 | 12.535 | 18.479 | P6(2)c |
| AS54-3 | FeBr$_2$ 0.927 BPDC 0.927 mmol | DMF anhydr. n-propanol | 90 | 109.98 | 90 | 12.019 | 15.286 | 14.399 | C2 |
| AS61-4 | FeBr$_2$ 0.927 mmol m-BDC 0.927 mmol | Pyridine anhydr. | 90 | 90 | 120 | 13.017 | 13.017 | 14.896 | P6(2)c |
| AS68-7 | FeBr$_2$ 0.927 mmol m-BDC 1.204 mmol | DMF anhydr. Pyridine | 90 | 90 | 90 | 18.3407 | 10.036 | 18.039 | Pca2$_1$ |
| Zn(ADC) | Zn(NO$_3$)$_2$.6H$_2$O 0.37 mmol H$_2$(ADC) 0.36 mmol | DMF Chlorobenzene | 90 | 99.85 | 90 | 16.764 | 9.349 | 9.635 | C2/c |
| MOF-12 Zn$_2$(ATC) | Zn(NO$_3$)$_2$.6H$_2$O 0.30 mmol H$_4$(ATC) 0.15 mmol | Ethanol | 90 | 90 | 90 | 15.745 | 16.907 | 18.167 | Pbca |
| MOF-20 ZnNDC | Zn(NO$_3$)$_2$.6H$_2$O 0.37 mmol H$_2$NDC 0.36 mmol | DMF Chlorobenzene | 90 | 92.13 | 90 | 8.13 | 16.444 | 12.807 | P2(1)/c |
| MOF-37 | Zn(NO$_3$)$_2$.6H$_2$O 0.20 mmol H$_2$NDC 0.20 mmol | DEF Chlorobenzene | 72.38 | 83.16 | 84.33 | 9.952 | 11.576 | 15.556 | P-1 |
| Zn(NDC) (DMSO) | Zn(NO$_3$)$_2$.6H$_2$O H$_2$NDC | DMSO | 68.08 | 75.33 | 88.31 | 8.631 | 10.207 | 13.114 | P-1 |
| Zn(NDC) | Zn(NO$_3$)$_2$.6H$_2$O H$_2$NDC | | 90 | 99.2 | 90 | 19.289 | 17.628 | 15.052 | C2/c |
| Zn(HPDC) | Zn(NO$_3$)$_2$.4H$_2$O 0.23 mmol H$_2$(HPDC) 0.05 mmol | DMF H$_2$O | 107.9 | 105.06 | 94.4 | 8.326 | 12.085 | 13.767 | P-1 |
| Co(HPDC) | Co(NO$_3$)$_2$.6H$_2$O 0.21 mmol H$_2$ (HPDC) 0.06 mmol | DMF H$_2$O/ethanol | 90 | 97.69 | 90 | 29.677 | 9.63 | 7.981 | C2/c |
| Zn$_3$(PDC)2.5 | Zn(NO$_3$)$_2$.4H$_2$O 0.17 mmol H$_2$(HPDC) 0.05 mmol | DMF/ClBz H$_2$0/TEA | 79.34 | 80.8 | 85.83 | 8.564 | 14.046 | 26.428 | P-1 |
| Cd$_2$ (TPDC)2 | Cd(NO$_3$)$_2$.4H$_2$O 0.06 mmol H$_2$(HPDC) 0.06 mmol | Methanol/CHP H$_2$O | 70.59 | 72.75 | 87.14 | 10.102 | 14.412 | 14.964 | P-1 |
| Tb(PDC)1.5 | Tb(NO$_3$)$_3$.5H$_2$O 0.21 mmol H$_2$(PDC) 0.034 mmol | DMF H$_2$O/ethanol | 109.8 | 103.61 | 100.14 | 9.829 | 12.11 | 14.628 | P-1 |
| ZnDBP | Zn(NO$_3$)$_2$.6H$_2$O 0.05 mmol dibenzylphosphate 0.10 mmol | MeOH | 90 | 93.67 | 90 | 9.254 | 10.762 | 27.93 | P2/n |
| Zn$_3$(BPDC) | ZnBr$_2$ 0.021 mmol | DMF | 90 | 102.76 | 90 | 11.49 | 14.79 | 19.18 | P21/n |

-continued

| MOF-n | Ingredients molar ratios M + L | Solvents | α | β | γ | a | b | c | Space Group |
|---|---|---|---|---|---|---|---|---|---|
| CdBDC | 4,4'BPDC 0.005 mmol Cd(NO$_3$)$_2$.4H$_2$O 0.100 mmol | DMF Na$_2$SiO$_3$ (aq) | 90 | 95.85 | 90 | 11.2 | 11.11 | 16.71 | P21/n |
| Cd-mBDC | H$_2$(BDC) 0.401 mmol Cd(NO$_3$)$_2$.4H$_2$O 0.009 mmol H$_2$(mBDC) 0.018 mmol | DMF MeNH$_2$ | 90 | 101.1 | 90 | 13.69 | 18.25 | 14.91 | C2/c |
| Zn$_4$OBNDC | Zn(NO$_3$)$_2$.6H$_2$O 0.041 mmol BNDC | DEF MeNH$_2$ H$_2$O$_2$ | 90 | 90 | 90 | 22.35 | 26.05 | 59.56 | Fmmm |
| Eu(TCA) | Eu(NO$_3$)$_3$.6H$_2$O 0.14 mmol TCA 0.026 mmol | DMF Chlorobenzene | 90 | 90 | 90 | 23.325 | 23.325 | 23.325 | Pm-3n |
| Tb(TCA) | Tb(NO$_3$)$_3$.6H$_2$O 0.069 mmol TCA 0.026 mmol | DMF Chlorobenzene | 90 | 90 | 90 | 23.272 | 23.272 | 23.372 | Pm-3n |
| Formate | Ce(NO$_3$)$_3$.6H$_2$O 0.138 mmol Formaic acid 0.43 mmol | H$_2$O Ethanol | 90 | 90 | 120 | 10.668 | 10.667 | 4.107 | R-3m |
| | FeCl$_2$.4H$_2$O 5.03 mmol Formic acid 86.90 mmol | DMF | 90 | 90 | 120 | 8.2692 | 8.2692 | 63.566 | R-3c |
| | FeCl$_2$.4H$_2$O 5.03 mmol Formic acid 86.90 mmol | DEF | 90 | 90 | 90 | 9.9364 | 18.374 | 18.374 | Pbcn |
| | FeCl$_2$.4H$_2$O 5.03 mmol Formic acid 86.90 mmol | DEF | 90 | 90 | 90 | 8.335 | 8.335 | 13.34 | P-31c |
| NO330 | FeCl$_2$.4H$_2$O 0.50 mmol Formic acid 8.69 mmol | formamide | 90 | 90 | 90 | 8.7749 | 11.655 | 8.3297 | Pnna |
| NO332 | FeCl$_2$.4H$_2$O 0.50 mmol Formic acid 8.69 mmol | DIP | 90 | 90 | 90 | 10.0313 | 18.808 | 18.355 | Pbcn |
| NO333 | FeCl$_2$.4H$_2$O 0.50 mmol Formic acid 8.69 mmol | DBF | 90 | 90 | 90 | 45.2754 | 23.861 | 12.441 | Cmcm |
| NO335 | FeCl$_2$.4H$_2$O 0.50 mmol Formic acid 8.69 mmol | CHF | 90 | 91.372 | 90 | 11.5964 | 10.187 | 14.945 | P21/n |
| NO336 | FeCl$_2$.4H$_2$O 0.50 mmol Formic acid 8.69 mmol | MFA | 90 | 90 | 90 | 11.7945 | 48.843 | 8.4136 | Pbcm |
| NO13 | Mn(Ac)$_2$.4H$_2$O 0.46 mmol Bezoic acid 0.92 mmol Bipyridine 0.46 mmol | Ethanol | 90 | 90 | 90 | 18.66 | 11.762 | 9.418 | Pbcn |
| NO29 MOF-0 Like | Mn(Ac)$_2$.4H$_2$O 0.46 mmol H$_3$BTC 0.69 mmol | DMF | 120 | 90 | 90 | 14.16 | 33.521 | 33.521 | P-1 |
| Mn(hfac)$_2$ (O$_2$CC$_6$H$_5$) | Mn(Ac)$_2$.4H$_2$O 0.46 mmol Hfac 0.92 mmol Bipyridine 0.46 mmol | Ether | 90 | 95.32 | 90 | 9.572 | 17.162 | 14.041 | C2/c |
| BPR43G2 | Zn(NO$_3$)$_2$.6H$_2$O 0.0288 mmol | DMF CH$_3$CN | 90 | 91.37 | 90 | 17.96 | 6.38 | 7.19 | C2/c |

-continued

| MOF-n | Ingredients molar ratios M + L | Solvents | α | β | γ | a | b | c | Space Group |
|---|---|---|---|---|---|---|---|---|---|
| BPR48A2 | H$_2$BDC 0.0072 mmol Zn(NO$_3$)$_2$ 6H$_2$O 0.012 mmol | DMSO Toluene | 90 | 90 | 90 | 14.5 | 17.04 | 18.02 | Pbca |
| BPR49B1 | H$_2$BDC 0.012 mmol Zn(NO$_3$)$_2$ 6H$_2$O 0.024 mmol | DMSO Methanol | 90 | 91.172 | 90 | 33.181 | 9.824 | 17.884 | C2/c |
| BPR56E1 | H$_2$BDC 0.048 mmol Zn(NO$_3$)$_2$ 6H$_2$O 0.012 mmol | DMSO n-propanol | 90 | 90.096 | 90 | 14.5873 | 14.153 | 17.183 | P2(1)/n |
| BPR68D10 | H$_2$BDC 0.024 mmol Zn(NO$_3$)$_2$ 6H$_2$O 0.0016 mmol | DMSO Benzene | 90 | 95.316 | 90 | 10.0627 | 10.17 | 16.413 | P2(1)/c |
| BPR69B1 | H$_3$BTC 0.0064 mmol Cd(NO$_3$)$_2$ 4H$_2$O 0.0212 mmol | DMSO | 90 | 98.76 | 90 | 14.16 | 15.72 | 17.66 | Cc |
| BPR73E4 | H$_2$BDC 0.0428 mmol Cd(NO$_3$)$_2$ 4H$_2$O 0.006 mmol | DMSO Toluene | 90 | 92.324 | 90 | 8.7231 | 7.0568 | 18.438 | P2(1)/n |
| BPR76D5 | H$_2$BDC 0.003 mmol Zn(NO$_3$)$_2$ 6H$_2$O 0.0009 mmol | DMSO | 90 | 104.17 | 90 | 14.4191 | 6.2599 | 7.0611 | Pc |
| BPR80B5 | H$_2$BzPDC 0.0036 mmol Cd(NO$_3$)$_2$.4H$_2$O 0.018 mmol | DMF | 90 | 115.11 | 90 | 28.049 | 9.184 | 17.837 | C2/c |
| BPR80H5 | H$_2$BDC 0.036 mmol Cd(NO$_3$)$_2$ 4H$_2$O 0.027 mmol | DMF | 90 | 119.06 | 90 | 11.4746 | 6.2151 | 17.268 | P2/c |
| BPR82C6 | H$_2$BDC 0.027 mmol Cd(NO$_3$)$_2$ 4H$_2$O 0.0068 mmol | DMF | 90 | 90 | 90 | 9.7721 | 21.142 | 27.77 | Fdd2 |
| BPR86C3 | H$_2$BDC 0.202 mmol Co(NO$_3$)$_2$ 6H$_2$O 0.0025 mmol | DMF | 90 | 90 | 90 | 18.3449 | 10.031 | 17.983 | Pca2(1) |
| BPR86H6 | H$_2$BDC 0.075 mmol Cd(NO$_3$)$_2$.6H$_2$O 0.010 mmol | DMF | 80.98 | 89.69 | 83.412 | 9.8752 | 10.263 | 15.362 | P-1 |
|  | H$_2$BDC 0.010 mmol Co(NO$_3$)$_2$ 6H$_2$O | NMP | 106.3 | 107.63 | 107.2 | 7.5308 | 10.942 | 11.025 | P1 |
| BPR95A2 | Zn(NO$_3$)$_2$ 6H$_2$O 0.012 mmol H$_2$BDC 0.012 mmol | NMP | 90 | 102.9 | 90 | 7.4502 | 13.767 | 12.713 | P2(1)/c |
| CuC$_6$F$_4$O$_4$ | Cu(NO$_3$)$_2$.2.5H$_2$O 0.370 mmol H$_2$BDC(OH)$_2$ 0.37 mmol | DMF Chlorobenzene | 90 | 98.834 | 90 | 10.9675 | 24.43 | 22.553 | P2(1)/n |
| Fe Formic | FeCl$_2$.4H$_2$O 0.370 mmol Formic acid 0.37 mmol | DMF | 90 | 91.543 | 90 | 11.495 | 9.963 | 14.48 | P2(1)/n |
| Mg Formic | Mg(NO$_3$)$_2$.6H$_2$O 0.370 mmol Formic acid 0.37 mmol | DMF | 90 | 91.359 | 90 | 11.383 | 9.932 | 14.656 | P2(1)/n |
| MgC$_6$H$_4$O$_6$ | Mg(NO$_3$)$_2$.6H$_2$O 0.370 mmol H$_2$BDC(OH)$_2$ 0.37 mmol | DMF | 90 | 96.624 | 90 | 17.245 | 9.943 | 9.273 | C2/c |
| Zn C$_2$H$_4$BDC MOF-38 | ZnCl$_2$ 0.44 mmol CBBDC 0.261 mmol | DMF | 90 | 94.714 | 90 | 7.3386 | 16.834 | 12.52 | P2(1)/n |

-continued

| MOF-n | Ingredients molar ratios M + L | Solvents | α | β | γ | a | b | c | Space Group |
|---|---|---|---|---|---|---|---|---|---|
| MOF-49 | ZnCl₂ 0.44 mmol m-BDC 0.261 mmol | DMF CH₃CN | 90 | 93.459 | 90 | 13.509 | 11.984 | 27.039 | P2/c |
| MOF-26 | Cu(NO₃)₂.5H₂O 0.084 mmol DCPE 0.085 mmol | DMF | 90 | 95.607 | 90 | 20.8797 | 16.017 | 26.176 | P2(1)/n |
| MOF-112 | Cu(NO₃)₂.2.5H₂O 0.084 mmol o-Br-m-BDC 0.085 mmol | DMF Ethanol | 90 | 107.49 | 90 | 29.3241 | 21.297 | 18.069 | C2/c |
| MOF-109 | Cu(NO₃)₂.2.5H₂O 0.084 mmol KDB 0.085 mmol | DMF | 90 | 111.98 | 90 | 23.8801 | 16.834 | 18.389 | P2(1)/c |
| MOF-111 | Cu(NO₃)₂.2.5H₂O 0.084 mmol o-BrBDC 0.085 mmol | DMF Ethanol | 90 | 102.16 | 90 | 10.6767 | 18.781 | 21.052 | C2/c |
| MOF-110 | Cu(NO₃)₂.2.5H₂O 0.084 mmol thiophene dicarboxylic 0.085 mmol | DMF | 90 | 90 | 120 | 20.0652 | 20.065 | 20.747 | R-3/m |
| MOF-107 | Cu(NO₃)₂.2.5H₂O 0.084 mmol thiophene dicarboxylic 0.085 mmol | DEF | 104.8 | 97.075 | 95.206 | 11.032 | 18.067 | 18.452 | P-1 |
| MOF-108 | Cu(NO₃)₂.2.5H₂O 0.084 mmol thiophene dicarboxylic 0.085 mmol | DBF/methanol | 90 | 113.63 | 90 | 15.4747 | 14.514 | 14.032 | C2/c |
| MOF-102 | Cu(NO₃)₂.2.5H₂O 0.084 mmol H₂(BDCCl₂) 0.085 mmol | DMF | 91.63 | 106.24 | 112.01 | 9.3845 | 10.794 | 10.831 | P-1 |
| Clbdc1 | Cu(NO₃)₂.2.5H₂O 0.084 mmol H₂(BDCCl₂) 0.085 mmol | DEF | 90 | 105.56 | 90 | 14.911 | 15.622 | 18.413 | P-1 |
| Cu(NMOP) | Cu(NO₃)₂.2.5H₂O 0.084 mmol NBDC 0.085 mmol | DMF | 90 | 102.37 | 90 | 14.9238 | 18.727 | 15.529 | P2(1)/m |
| Tb(BTC) | Tb(NO₃)₃.5H₂O 0.033 mmol H₃BTC 0.033 mmol | DMF | 90 | 106.02 | 90 | 18.6986 | 11.368 | 19.721 | |
| Zn₃(BTC)₂ Honk | ZnCl₂ 0.033 mmol H₃BTC 0.033 mmol | DMF Ethanol | 90 | 90 | 90 | 26.572 | 26.572 | 26.572 | Fm-3m |
| Zn₄O(NDC) | Zn(NO₃)₂.4H₂O 0.066 mmol 14NDC 0.066 mmol | DMF ethanol | 90 | 90 | 90 | 41.5594 | 18.818 | 17.574 | aba2 |
| CdTDC | Cd(NO₃)₂.4H₂O 0.014 mmol thiophene 0.040 mmol DABCO 0.020 mmol | DMF H₂O | 90 | 90 | 90 | 12.173 | 10.485 | 7.33 | Pmma |
| IRMOF-2 | Zn(NO₃)₂.4H₂O 0.160 mmol o-Br-BDC 0.60 mmol | DEF | 90 | 90 | 90 | 25.772 | 25.772 | 25.772 | Fm-3m |
| IRMOF-3 | Zn(NO₃)₂.4H₂O 0.20 mmol H₂N-BDC 0.60 mmol | DEF Ethanol | 90 | 90 | 90 | 25.747 | 25.747 | 25.747 | Fm-3m |
| IRMOF-4 | Zn(NO₃)₂.4H₂O 0.11 mmol | DEF | 90 | 90 | 90 | 25.849 | 25.849 | 25.849 | Fm-3m |

| MOF-n | Ingredients molar ratios M + L | Solvents | α | β | γ | a | b | c | Space Group |
|---|---|---|---|---|---|---|---|---|---|
| IRMOF-5 | [C$_3$H$_7$O]$_2$-BDC 0.48 mmol<br>Zn(NO$_3$)$_2$.4H$_2$O 0.13 mmol | DEF | 90 | 90 | 90 | 12.882 | 12.882 | 12.882 | Pm-3m |
| IRMOF-6 | [C$_5$H$_{11}$O]$_2$-BDC 0.50 mmol<br>Zn(NO$_3$)$_2$.4H$_2$O 0.20 mmol | DEF | 90 | 90 | 90 | 25.842 | 25.842 | 25.842 | Fm-3m |
| IRMOF-7 | [C$_2$H$_4$]-BDC 0.60 mmol<br>Zn(NO$_3$)$_2$.4H$_2$O 0.07 mmol | DEF | 90 | 90 | 90 | 12.914 | 12.914 | 12.914 | Pm-3m |
| IRMOF-8 | 1,4NDC 0.20 mmol<br>Zn(NO$_3$)$_2$.4H$_2$O 0.55 mmol | DEF | 90 | 90 | 90 | 30.092 | 30.092 | 30.092 | Fm-3m |
| IRMOF-9 | 2,6NDC 0.42 mmol<br>Zn(NO$_3$)$_2$.4H$_2$O 0.05 mmol | DEF | 90 | 90 | 90 | 17.147 | 23.322 | 25.255 | Pnnm |
| IRMOF-10 | BPDC 0.42 mmol<br>Zn(NO$_3$)$_2$.4H$_2$O 0.02 mmol | DEF | 90 | 90 | 90 | 34.281 | 34.281 | 34.281 | Fm-3m |
| IRMOF-11 | BPDC 0.012 mmol<br>Zn(NO$_3$)$_2$.4H$_2$O 0.05 mmol | DEF | 90 | 90 | 90 | 24.822 | 24.822 | 56.734 | R-3m |
| IRMOF-12 | HPDC 0.20 mmol<br>Zn(NO$_3$)$_2$.4H$_2$O 0.017 mmol | DEF | 90 | 90 | 90 | 34.281 | 34.281 | 34.281 | Fm-3m |
| IRMOF-13 | HPDC 0.12 mmol<br>Zn(NO$_3$)$_2$.4H$_2$O 0.048 mmol | DEF | 90 | 90 | 90 | 24.822 | 24.822 | 56.734 | R-3m |
| IRMOF-14 | PDC 0.31 mmol<br>Zn(NO$_3$)$_2$.4H$_2$O 0.17 mmol | DEF | 90 | 90 | 90 | 34.381 | 34.381 | 34.381 | Fm-3m |
| IRMOF-15 | PDC 0.12 mmol<br>Zn(NO$_3$)$_2$.4H$_2$O 0.063 mmol | DEF | 90 | 90 | 90 | 21.459 | 21.459 | 21.459 | Im-3m |
| IRMOF-16 | TPDC 0.025 mmol<br>Zn(NO$_3$)$_2$.4H$_2$O 0.0126 mmol<br>TPDC 0.05 mmol | DEF<br>NMP | 90 | 90 | 90 | 21.49 | 21.49 | 21.49 | Pm-3m |
| | FeBr$_2$ 0.927 mmol<br>BDC 0.927 mmol | DMF<br>1 Propanol | | | | | | | |
| | FeCl$_3$.6H$_2$O<br>BDC 1.23 mmol | DMF<br>Ethanol | | | | | | | |
| | Mg(NO$_3$)$_2$.6H$_2$O<br>DHBC 0.185 mmol | DMF | | | | | | | |
| | Zn(NO$_3$)$_2$.4H$_2$O 0.20 mmol<br>DHBC 0.10 mmol | DMF<br>i-Propanol | 90 | 90 | 120 | 25.9 | 25.9 | 6.8 | R-3 |
| | Mn(ClO$_4$)$_2$.6H$_2$O<br>DHBC 0.065 mmol | DMF<br>i-Propanol | | | | | | | |
| | Tb(NO$_3$)$_3$.5H$_2$O<br>DHBC 0.050 mmol | DMF<br>i-Propanol | | | | | | | |

ADC Acetylene dicarboxylic acid
NDC Naphtalene dicarboxylic acid
BDC Benzene dicarboxylic acid
ATC Adamantane tetracarboxylic acid
BTC Benzene tricarboxylic acid
BTB Benzene tribenzoate
MTB Methane tetrabenzoate
ATB Adamantane tetrabenzoate
ADB Adamantane dibenzoate
BPDC 4,4-Biphenyldicarboxylic acid
DHBC 2,5-Dihydroxyterephthalic acid Examples for the synthesis of these materials as such can, for example, be found in: J. Am. Chem. Soc. 123 (2001) pages 8241 seq. or in Acc. Chem. Res. 31 (1998) pages 474 seq., which are fully encompassed in the present application.

The separation of the framework materials from the mother liquor of the crystallization can be achieved by procedures known in the art such as solid-liquid separations, centrifugation, extraction, filtration, membrane filtration, cross-flow filtration, flocculation using flocculation adjuvants (non-ionic, cationic and anionic adjuvants) or by the addition of pH shifting additives such as salts, acids or bases, by flotation, as well as by evaporation of the mother liquor at elevated temperature and/or in vacuo and concentrating of the solid. The material obtained in this step is typically a fine powder and cannot be used for most practical applications, e.g., in catalysis, where shaped bodies are required.

The separated framework materials may be compounded, melted, extruded, co-extruded, pressed, spinned, foamed and granulated according to processes known within the processing of plastics, respectively.

One advantage of the process according to the present invention is that the polyoxyalkylene alcohols obtainable have a low, preferred degree of alkoxylation. The alcohols comprise generally 1 to 5 alkoxy units, preferably 1 to 3 alkoxy units, more preferably 1 or 2 alkoxy units, in particular 1 alkoxy unit.

The polyoxyalkylene alcohols which are obtainable according to the present invention lend themselves for a number of applications. Non-limiting examples include polyurethane-foams, lubricating liquids, hydraulic fluid, carrier liquid, tenside and flotation oil.

The invention is now illustrated by way of the following examples which are not intended to limit the scope of the present invention.

EXAMPLES

Example 1

Preparation of MOF-5

| Starting Material | Molar Amount | Calculated | Experimental |
|---|---|---|---|
| terephthalic acid | 12.3 mmol | 2.04 g | 2.34 g |
| Zinc nitrate-tetra hydrate | 36.98 mmol | 9.67 g | 9.66 g |
| Diethylformamide (Merck) | 2568.8 mmol | 282.2 g | 282.2 g |

The above-mentioned amounts of the starting materials were dissolved in a beaker in the order diethylformamide, terephthalic acid and zinc nitride. The resulting solution was transferred into two autoclaves (250 ml) with teflon covered inner walls.

The crystallization occurred at 105° C. over 68 hours. Subsequently, the orange solvent, together with the red crystals, was transferred into a beaker, and the suspension is filtered unter an N2 atmosphrere. The suspension was washed with 3 ml of chloroform before being activated in vacuo. There were obtained 2.3 g of product.

Example 2

2,5-Dihydroxyterephthalic acid (19 mg, 0,10 mmol) and $Zn(NO_3)_2 \cdot 4H_2O$ (53 mg, 0.20 mmol) were dissolved in a mixed solution of DMF (2.0 mL), PrOH(0.10 mL) and water (0.10 mL), which was placed in a pyrex tube (10 mm×70 mm). The tube was frozen and evacuated, and flame sealed under vacuum. The tube was heated to 105° C. at 2° C./min, held for 20 hours, then cooled to room temperature at 2° C./min. Yellow needle crystals were collected and washed with DMF (3×5 mL). Yield: 26 mg, 81% based on the 2,5-dihydroxyterephthalic acid.

Example 3

Alkoxylation of i-Tridecanol N with Propylene Oxide i-Tridecanol N (4,8 g corresponding to 0.024 mole) and 0.8 g of the catalyst prepared according to Example 1 were given into an autoclave. Subsequently, the autoclave was filled with 12 g propylene oxide (0.207 mole). The reaction was carried out at 135° C., and in total 9.4 mole propylene oxide/mole starting alcohol were reacted to obtain 18.7 g of product.

Example 4

Alkoxylation of 2-Propylheptanol with Ethylene Oxide

2-Propylheptanol (12.67 g corresponding to 0.08 mole) and 0.49 g of the catalyst prepared according to Example 2 were given into an autoclave. Subsequently, the autoclave was filled with 7.05 g ethylene oxide (0.16 mole). The reaction was carried out at 135° C. over 10 h, before the autocalve was cooled to 50° C., at which temperature the reaction mixture was stirred for another 3 h. In total 3.74 mole ethylene oxide/mole starting alcohol were reacted, to obtain 27.98 g of product.

The invention claimed is:

1. A process, which comprises:
alkoxylating a monool with at least one alkoxylating agent to obtain a polyoxyalkylene alcohol comprising 1 to 5 alkoxy units in the presence of a catalyst comprising a metallo-organic framework material of metal ions and at least one bidentate coordinately bound organic ligands, wherein the bidentate coordinately bound organic ligands are selected from the group consisting of an hydroxy-substituted aromatic mononuclear polycarboxylic acid, an hydroxyl-substituted polynuclear aromatic polycarboxylic acid, an hydroxyl-substituted aromatic mononuclear polycarboxylic acid comprising at least one heteroatom, an hydroxy-substituted aromatic polynuclear polycarboxylic acid comprising at least one heteroatom, and combinations thereof.

2. The process according to claim 1, wherein the metal ion is selected from the group consisting of any one elements of Groups 1 to 18, and combinations thereof of the periodic table of the elements.

3. The process according to claim 1, wherein the bidentate organic ligand is 2,5-dihydroxyterephthalic acid.

4. The process according to claim 1, wherein the metallo-organic framework material exhibits a specific surface area, as determined via adsorption, of >20 m$^2$/g.

5. The process according to claim 1, wherein the alkoxylation agent is selected from the group consisting of a monofunctional epoxide having 2 to 30 carbon atoms, a multifunctional epoxide having 2 to 30 carbon atoms, and mixtures thereof.

6. The process according to claim 5, wherein the epoxide is selected from the group consisting of ethylene oxide, propylene oxide, a butylene oxide, and mixtures thereof.

7. A method of using an alcohol obtained by the process as claimed in claim 1, which comprises:
preparing a tenside, a flotation oil, a lubricating liquid, a hydraulic fluid, a carrier liquid or a polyurethane foam comprising the alcohol.

8. The method of using according to claim 7 where the alcohol is selected from monools of linear and branched alkyl groups having 1 to 30 carbon atoms, which alkyl groups may carry one or more aryl substituents, of homo- and polynuclear aromatic groups having 4 to 30 carbon atoms, which aromatic groups may carry one or more alkyl substituents, and of linear and branched alkenyl groups having 2 to 30 carbon atoms and which alkenyl groups may carry one or more aryl substituents.

* * * * *